US008268566B2

(12) United States Patent
Mitsuhashi et al.

(10) Patent No.: US 8,268,566 B2
(45) Date of Patent: Sep. 18, 2012

(54) ENHANCED FC RECEPTOR-MEDIATED TUMOR NECROSIS FACTOR SUPERFAMILY MRNA EXPRESSION IN PERIPHERAL BLOOD LEUKOCYTES IN PATIENTS WITH RHEUMATOID ARTHRITIS (75) Inventors: Masato Mitsuhashi, Irvine, CA (US); Katsuya Endo, Ibaraki (JP); Kazuhiko Obara, Ibaraki (JP); Hiroshi Izutsu, Ibaraki (JP); Shuji Ohta, Ibaraki (JP)

(73) Assignees: Hitachi Chemical Research Center, Inc., Irvine, CA (US); Hitachi Chemical Co., Ltd., Shinjuku-ku, Tokyo (JP)

( * ) Notice: Subject to any disclaimer, the term of this patent is extended or adjusted under 35 U.S.C. 154(b) by 100 days.

(21) Appl. No.: 12/743,220

(22) PCT Filed: Nov. 11, 2008

(86) PCT No.: PCT/US2008/083136
§ 371 (c)(1),
(2), (4) Date: Jun. 30, 2010

(87) PCT Pub. No.: WO2009/070442
PCT Pub. Date: Jun. 4, 2009

(65) Prior Publication Data
US 2010/0279296 A1 Nov. 4, 2010

Related U.S. Application Data (63) Continuation-in-part of application No. 12/296,423, filed as application No. PCT/US2007/008559 on Apr. 5, 2007, now abandoned.

(60) Provisional application No. 61/002,967, filed on Nov. 14, 2007, provisional application No. 60/790,511, filed on Apr. 7, 2006.

(51) Int. Cl.
C12Q 1/68 (2006.01)
C12N 5/078 (2010.01)
A61K 39/395 (2006.01)
A61K 38/17 (2006.01)
A61P 19/02 (2006.01)
C07K 14/425 (2006.01)

(52) U.S. Cl. .... 435/6.17; 435/372; 530/350; 424/133.1; 514/16.6

(58) Field of Classification Search .................. None
See application file for complete search history.

(56) References Cited

U.S. PATENT DOCUMENTS

| 4,880,548 | A | 11/1989 | Pall et al. |
| 4,925,572 | A | 5/1990 | Pall |
| 5,427,916 | A | 6/1995 | Gewirtz et al. |
| 5,474,909 | A | 12/1995 | Connors et al. |
| 5,683,698 | A | 11/1997 | Chavali et al. |
| 6,692,916 | B2 | 2/2004 | Bevilacqua |
| 7,332,631 | B2 | 2/2008 | Hogarth et al. |
| 7,741,023 | B2 | 6/2010 | Mitsuhashi |
| 7,838,239 | B2 | 11/2010 | Mitsuhashi et al. |
| 2001/0006789 | A1 | 7/2001 | Maino et al. |
| 2001/0051344 | A1 | 12/2001 | Shalon et al. |
| 2002/0006613 | A1 | 1/2002 | Shyjan |
| 2002/0048566 | A1 | 4/2002 | El-Deiry et al. |
| 2002/0106684 | A1 | 8/2002 | Kopreski |
| 2003/0138781 | A1 | 7/2003 | Whitehead |
| 2003/0148345 | A1 | 8/2003 | Kopreski |
| 2004/0072268 | A1 | 4/2004 | Shiekhattar |
| 2004/0152204 | A1 | 8/2004 | Gauthier |
| 2004/0265864 | A1 | 12/2004 | Mitsuhashi |
| 2007/0196835 | A1 | 8/2007 | Bankaitis-Davis et al. |
| 2008/0206761 | A1 | 8/2008 | Mitsuhashi |
| 2008/0261207 | A1 | 10/2008 | Mitsuhashi |
| 2009/0011410 | A1 | 1/2009 | Mitsuhashi |
| 2009/0215064 | A1 | 8/2009 | Mitsuhashi et al. |
| 2009/0298071 | A1 | 12/2009 | Mitsuhashi et al. |
| 2009/0311684 | A1 | 12/2009 | Mitsuhashi et al. |

FOREIGN PATENT DOCUMENTS

| EP | 1243274 | 9/2002 |
| JP | 2002-058495 | 2/2002 |
| JP | 2002-223753 | 8/2002 |
| WO | WO 98/22825 | 5/1998 |
| WO | 98/47004 | 10/1998 |
| WO | WO 02/066637 | 8/2002 |
| WO | WO 03/030719 | 4/2003 |
| WO | 03/040404 | 5/2003 |
| WO | 03/059333 | 7/2003 |
| WO | 03/090694 | 11/2003 |

(Continued)

OTHER PUBLICATIONS

Pachot et al. Increased tumor necrosis factor-alpha mRNA expression in whole blood from patients with rheumatoid arthritis: reduction after infliximab treatment does not predict response. J Rheumatol. Nov. 2007;34(11):2158-61. Epub Sep. 15, 2007.*
Chaudhary et al., Prediction of response to infliximab in Crohn's disease, Digestive and Liver Disease, 2005, vol. 37, Issue 8, pp. 559-563.
Christoph Hartel et al., Delayed Cytokine mRNA Expression Kinetics after T-Lymphocyte Costimulation: A Quantitative Measure of the Efficacy of Cyclosporin A-based Immunosuppression, Clinical Chemistry, 2002, vol. 48, Issue 12, pp. 2225-2231.
European Patent Office, EP Search Report for EP 06772657.0, Dec. 2, 2008.
European Patent Office, European Search Report for EP 05819894.6, Mar. 6, 2009.
European Search Report, EP Search Report for EP 07755012.7, May 8, 2009.

(Continued)

Primary Examiner — David Romeo
(74) Attorney, Agent, or Firm — Knobbe Martens Olson & Bear, LLP (57) ABSTRACT A method for predicting patient responsiveness to rheumatoid arthritis treatments involving altering expression of tumor necrosis factor superfamily ("TNFSF")-2, TNFSF-8, or TNFSF-15 is disclosed. A method for monitoring the effectiveness of such therapy is also disclosed. Furthermore, a method of screening compounds for use in the treatment of rheumatoid arthritis is disclosed. A method of monitoring the disease state over time in rheumatoid arthritis patients is also disclosed.

5 Claims, 3 Drawing Sheets

FOREIGN PATENT DOCUMENTS

| WO | 03/099312 | 12/2003 |
|---|---|---|
| WO | WO 2004/004792 | 1/2004 |
| WO | 2005/115115 | 12/2005 |
| WO | WO 2006/045053 | 4/2006 |
| WO | WO 2006/076492 | 7/2006 |
| WO | WO 2006/110091 | 10/2006 |
| WO | 2006/116721 | 11/2006 |
| WO | WO 2006/133399 | 12/2006 |
| WO | WO 2007/038501 | 4/2007 |
| WO | WO 2007/117589 | 10/2007 |
| WO | WO 2007/117611 | 10/2007 |
| WO | WO 2007/133551 | 11/2007 |
| WO | 2008/106451 | 9/2008 |
| WO | WO 2009/070442 | 6/2009 |

OTHER PUBLICATIONS

Flores Mona G et al., In vitro evaluation of the effects of candidate immunosuppressive drugs: flow cytometry and quantitative real-time PCR as two independent and correlated read-outs, Journal of Immunological Methods, Jun. 2004, vol. 289, Issue 1-2, pp. 123-135.

Fujikado et al., Identification of arthritis related gene clusters by microarray analysis of two independent mouse models for rheumatoid arthritis, Arthritis Research and Therapy, 2006, vol. 8, pp. 1-13.

Giacomelli et al., Combination therapy with cyclosporine and methotrexate in patients with early rheumatoid arthritis soon inhibits TNF production without decreasing TNF mRNA level. An in vivo and in vitro study, Clinical and Experimental Rheumatology, 2002, vol. 20, pp. 365-372.

Haertel C et al., Dose-dependent Immunomodulatory Effects of Acetylsalicylic Acid and Indomethacin in Human Whole Blood: Potential Role of Cyclooxygenase-2 Inhibition, Scandinavian Journal Immunology, Oct. 2004, vol. 60, Issue 4, pp. 412-420.

International Search Report, International Application No. PCT/US08/83136, Jul. 17, 2009.

International Search Report, International Application No. PCT/US07/08559, Sep. 4, 2008.

International Searching Authority, International Search Report for PCT/US2005/037925, Patent Cooperation Treaty, Feb. 21, 2007.

Klein N J et al., Ex-Vivo Assessment of Candidate Anti-Inflammatory Agents in the Treatment of Gram Negative Sepsis, Immunology and Infectious Diseases, 1994, vol. 4, Issue 1, pp. 33-35.

Mascheretti et al., Pharmacogenetic investigation of the TNF/TNF-receptor system in patients with chronic active Crohn's disease treated with infliximab, The Pharmacogenomics Journal, 2002, vol. 2, Issue 2, pp. 127-136.

Plevy et al., A Role for TNF-α and Mucosal T Helper-1 Cytokines in the Pathogenesis of Crohn's Disease, The Journal of Immunology, 1997, vol. 159, Issue 12, pp. 6276-6282.

Shetty et al., Pharmacogenomics of Response to Anti-Tumor Necrosis Factor Therapy in Patients with Crohn's Disease, American Journal of Pharmacogenomics, 2002, vol. 2, Issue 4, pp. 215-221.

Warzocha et al., Tumor Necrosis Factor Ligand-Receptor System Can Predict Treatment Outcome in Lymphoma Patients, Journal of Clinical Oncology, 1997, vol. 15, pp. 499-508.

Wen et al, TL1A-induced NF-kB Activation and c-IAP2 Production prevent DR3-mediated Apoptosis in TF-1 Cells, The Journal of Biological Chemistry, Oct. 3, 2003; 278, vol. 46, pp. 39251-39258.

Wouters et al., Inter- and intraindividual variation of endotoxin- and Beta(1->3)-glucan-induced cytokine responses in a whole blood assay, Toxicology and Industrial Health, 2002, vol. 18, pp. 15-27.

Yamazaki et al., Single nucleotide polymorphisms in TNFSF15 confer susceptibility to Crohn's disease, Human Molecular Genetics, 2005, vol. 14, Issue 22, pp. 3499-3506.

See et al., Increased Tumor Necrosis Factor Alpha (TNF-( ) and Natural Killer Cell (NK) Function Using an Integrative Approach in Late Stage Cancers, Immunological Investigations, 2002, vol. 31, Issue 2, pp. 137-153.

Snyder et al., Gene expression profiling after irradiation: clues to understanding acute and persistent responses?, Cancer and Metastatic Reviews, Aug. 1, 2004, vol. 23, Issue 3-4, pp. 259-268.

Spencer et al., Quantitative Analysis of Constitutive and 2,3,7,8-Tetrachlorodibenzo-p-dioxin-induced Cytochrome P450 1B1 Expression in Human Lymphocytes, Cancer Epidemiology, Biomarkers & Prevention, Feb. 1999, vol. 8, pp. 139-146.

Stuhmer et al., Ectopic expression of the Dix genes induces glutamic acid decarboxylase and Dix expression, Development, 2002, vol. 129, pp. 245-252.

Toussirot et al., "The use of TNF-α blocking agents in rheumatoid arthritis: an overview," Expert Opinion on Pharmacotherapy, Ashley, London, UK, Mar. 1, 2004, vol. 5(3), pp. 581-594, XP008074575, ISSN: 1465-6566.

Traganos et al., Effects of genistein on the growth and cell cycle progression of normal human lymphocytes and human leukemic MOLT-4 and HL-60 cells, Cancer Res., 1992, vol. 52, Issue 22, pp. 6200-6208.

Verneris et al., Resistance of ex vivo expanded CD3+CD56+ T cells to Fas-mediated apoptosis, Cancer Immunol Immunother, 2000, vol. 49, pp. 335-345.

Vickers et al., Precision cut organ slices to investigate target organ injury, Expet Opin Metab Toxicol, 2005, vol. 1, Issue 4, pp. 687-699.

Villunger et al., p53- and Drug-Induced Apoptotic Responses Mediated by BH3-Only Proteins Puma and Noxa, Science, Nov. 7, 2003, vol. 302, pp. 1036-1038.

Wei et al., Inhibition of tumor promoter-induced hyrogen peroxide formation in vitro and in vivo by genistein, Nutr Cancer, 1993, vol. 20, Issue 1, pp. 1-12.

Wyttenbach et al., P53—Dependent apoptosis induced by DNA damage and its relation to ERK signalling in sympathetic neurones, Society for Neuroscience Abstract Viewer and Itinerary Planner, 2003, pp. 147.3.

Yu et al., PUMA Induces the Rapid Apoptosis of Colorectal Cancer Cells, Mol. Cell., Mar. 2001, vol. 7, pp. 673-682.

Zhao et al., y-Radiation-induced G2 Delay, Apoptosis, and p53 Response as Potential Susceptibility Markers for Lung Cancer, Cancer Research, Nov. 1, 2001, vol. 61, pp. 7819-7824.

Ames et al. Are Vitamin and Mineral Deficiencies a Major Cancer Risk?, Nature Sep. 2002, 694-704.

Aggarwal et al., The Role of TNF and Its Family Members in Inflammation and Cancer: Lessons From Gene Deletion, Curr. Drug Targets Inflamm. Allergy, vol. 1(4): 327-341 (2002).

Chiaretti et al., Gene expression profile of adult T-cell acute lymphocytic leukemia identifies distinct subsets of patients with different response to therapy and survival, Blood, vol. 103(7): 2771-2778 (2004).

Hess et al., The Hydroxylamine of Sulfamethoxazole Syngerizes with FK506 and Cyclosporin A, Inhibiting T-Cell Proliferation, JPET 281(1): 540-546 (1997).

Leung et al., Expression Profiling Identifies Chemokine (C-C Motif) Ligand 18 as an Independent Prognostic Indicator in Gastric Cancer, Gastroenterology vol. 127:457-469 (2004).

Min et al., Prognostic Significance of Fas (CD95) and Trail Receptors (DR4/DR5) Expression in Acute Myelogenous Leukemia, Leukemia Research vol. 28: 359-365 (2004).

Moran et al., RANTES Expression is a Predictor of Survival in Stage I Lung Adenocarcinoma, Clin. Cancer Res., vol. 8:3803-3812 (2002).

Mehmut et al., Fas ligand and TNF-related Apoptosis-inducing ligand induction on infiltrating lymphocytes in bladder carcinoma by Bacillus Calmette-Guerin Treatment., Urologia Intl. 75:80-87 (2005).

Spierings et al., Expression of TRAIL and TRAIL Death Receptors in Stage III Non-small Cell Lung Cancer Tumors, Clin. Cancer Res. vol. 9: 3397-3405 (2003).

Strater et al., Expression of TRAIL and TRAIL Receptors in Colon Carcinoma: TRAIL-R1 is an Independent Prognostic Parameter, Clin. Cancer Res. vol. 8:3734-3740 (2002).

Fukumi et al., Differential responses of Bcl-2 family genes to etoposide in chronic myeloid leukemia K562 cells., Mol. and Cell. Biochem. vol. 206:43-50 (2000).

Younes et al., Clinical Implications of the Tumor Necrosis Factor Family in Benign and Malignant Hematologic Disorders., Cancer vol. 98: 458-467 (2003).

Younes et al., Emerging Applications of the Tumor Necrosis Factor Family of Ligands and Receptors in Cancer Therapy, J. Clin. Oncol. vol. 21:3526-3534 (2003).

International Search Report and Written Opinion of the International Searching Authority for International Application for International Application No. PCT/US2007/08597 mailed on Jun. 4, 2008.

International Search Report and Written Opinion of the International Searching Authority for International Application for International Application No. PCT/US2006/022427 mailed on Sep. 21, 2006.

International Search Report for International Application No. PCT/US2008/083136 mailed on Jul. 17, 2009.

Extended European Search Report issued in European Patent Application No. 08853839.2 on Mar. 11, 2011.

Office Action issued in European Patent Application No. 08853839.2 on Nov. 18, 2011.

Office Action issued in Japan Patent Application No. 2007-538070 on Aug. 10, 2010.

Office Action issued in Japan Patent Application No. 2008-509198 on Mar. 15, 2011.

Office Action issued in Japan Patent Application No. 2008-509198 on Oct. 25, 2011.

Office Action issued in Japan Patent Application No. 2009-504317 on Jul. 12, 2011.

International Search Report and Written Opinion for International Application No. PCT/US07/08559 mailed on Sep. 4, 2008.

Charles et al., Regulation of Cytokines, Cytokine Inhibitors, and Acute-Phase Proteins Following Anti-TNF-alpha Therapy in Rheumatoid Arthritis, J Immunol. vol. 163: 1521-1528 (1999).

Adam et al., Immune responses in cancer, Pharmacology & Therapeutics, 2003, vol. 99, pp. 113-132.

Amundson et al., Identification of Potential mRNA Biomarkers in Peripheral Blood Lymphocytes for Human Exposure to Ionizing Radiation, Radiation Research, 2000, vol. 154, pp. 342-346.

Anderson et al., Mutations of the homeobox genes Dlx-1 and Dlx-2 disrupt the striatal subventricular zone and differentiation of late born striatal neurons, Neuron, Jul. 1997, vol. 19, pp. 27-37.

Bornkamm et al., Molecular virology of Epstein-Barr virus, Phil. Trans. R. Soc. Lond. B., 2001, pp. 437-459.

Bush et al., Cancer Chemoresistance: The relationship Between P53 and Multidrug Transporters, Int J Cancer, 2002, vol. 98, pp. 323-330.

Chen et al., Inhibition of Ultraviolet B-Induced c-fos Gene Expression and p38 Mitogen-Activated Protein Kinase Activation by (-)-Epigallocatechin Gallate in a Human Keratinocyte Cell Line, Molecular Carcinogenesis, Feb. 1999, vol. 24, Issue 2, pp. 79-84.

Cheung et al., Natural variation in human gene expression assessed in lymphoblastoid cells, Nature Genetics, 2003, vol. 33, pp. 422-425.

Cline et al., Prediction of in Vivo Cytotoxicity of Chemotherapeutic Agents by Their Effect on Malignant Leukocytes in Vitro, Blood, Aug. 1967, vol. 30, Issue 2, pp. 176-188.

Cobb et al., Sepsis gene expression profiling: Murine splenic compared with hepatic responses determined by using complementary DNA microarrays, Crit Care Med, 2002, vol. 30, Issue 12, pp. 2711-2721.

De Kanter et al., A new techinique for preparing precision cut slices from small intestine and colon for drug biotransformation studies, Journal of Pharmacological and Toxicological Methods, 2005, vol. 51.

Dingemans et al., Expression of DNA Topoisomerase IIa and Topoisomerase IIb Genes Predicts Survival and Response to Chemotherapy in Patients with Small Cell Lung Cancer, Clinical Cancer Research, Aug. 1999, vol. 5, pp. 2048-2058.

Encyclopaedia Britannica Online, lymphocyte, In Encyclopaedia Britannica Britannica htt:www.search.eb.com/eb/article-9049513, Aug. 5, 2010.

Eyupoglu et al., Suberoylanilide hydroxamic acid (SAHA) has potent anti-glioma properties in vitro, ex vivo and in vivo, Journal of Neurochemistry, May 2005, vol. 93, Issue 4, pp. 992-999.

Fischer et al., Melatonin reduces UV-induced reactive oxygen species in a dose-dependent manner in IL-3-stimulated leukocytes, Journal of Pineal Research, 2001, vol. 31, Issue 1, pp. 39-45.

Ghosh et al., Anti-TNF therapy in Crohn's disease, Novartis Foundation Symposium, 2004, vol. 263, pp. 193-218.

Hamazumi, Gene Expression Analysis Using DNA Chips, High-Tech Information, 2003, Issue 148, pp. 27-31.

Han et al., Expression of bbc3, a pro-apoptotic BH2-only gene, is regulated by diverse cell death and survival signals, Proc. Natl. Acad. Sci. USA, Sep. 25, 2001, vol. 98, Issue 30, pp. 11318-11323.

Harrigan et al., DNA adduct formation in precision-cut rat liver and lung slices exposed to Benzo(a)pyrene, Toxicological Sciences, Feb. 2004, vol. 77, Issue 2, pp. 307-314.

Hoque et al., PUMA in Head and Neck Cancer, Cancer Letters, 2003, vol. 199, pp. 75-81.

Hoshikawa et al., Hypoxia induces different genes in the lungs of rats compared with mice, Physiol Genomics, 2003, vol. 12, pp. 209-219.

Ise et al., Analysis of cell viability and differential activity of mouse hepatocytes under 3D and 2D culture in agarose gel, Biotechnology Letters, 1999, vol. 21, pp. 209-213.

Iyer et al., p300 regulates p53-dependent apoptosis after DNA damage in colorectal cancer cells by modulation of PUMA/p21 levels, PNAS, May 11, 2004, vol. 101, Issue 19, pp. 7386-7391.

Juhasz et al., Quantification of Chemotherapeutic Target Gene mRNA Expression in Human Breast Cancer Biopsies: Comparison of Real-Time Reverse Transcription-PCR vs. Relative Quantification Reverse Transcription-PCR Utilizing DNA Sequencer Analysis of PCR Product, Journal of Clinical Laboratory Analysis, 2003, vol. 17, pp. 184-194.

Karlan et al., The role of genetic testing for cancer susceptibility in gynecologic practice, Obstet Gynecol., 2007, vol. 110, Issue 1, pp. 155-167.

Kasper et al., Precision cut tissue slices of the liver as morphological tool for investigation of apoptosis, In Vivo (ATTIKI), Mar. 2005, vol. 19, Issue 2, pp. 423-431.

Kastbom et al., "Fcγ Receptor Type IIIA Genotype and Response to Tumor Necrosis Factor α-Blocking Agents in Patients with Rheumatoid Arthritis," Arthritis & Rheumatism, Feb. 2007, vol. 56(2), pp. 448-452, XP002625046, ISSN: 0004-3591.

Kitahara et al., Classification of Sensitivity or Resistance of Cervical Cancers to Ionizing Radiation According to Expression Profiles of 62 Genes Selected by cDNA Microarray Analysis, Neoplasia, 2002, vol. 4, Issue 4, pp. 295-303.

Konigshoff et al., HER-2/neu Gene Copy Number Quantified by Real-Time PCR: Comparison of Gene Amplification, Heterozygosity, and Immunohistochemical Status in Breast Cancer Tissue, Clinical Chemistry, 2003, vol. 49(2), pp. 219-229.

Kostyuchenko et al., Effects of N-acylethanolamines and various antimitotic agents on apoptotic DNA fragmentation in conventionally normal and tumor tissue of human adrenals, Experimental Oncology, Sep. 2005, vol. 27, Issue 3, pp. 215-219.

Liu et al., Bax conformational change is a crucial step for PUMA-mediated apoptosis in human leukemia, Biochemical and Biophysical Research Communications, Oct. 24, 2003, vol. 310, Issue 3, pp. 956-962.

MacLeod et al., p53-Dependent and independent expression of p21 during cell growth, differentiation, and DNA damage, Genes & Development, 1995, vol. 9, pp. 935-944.

Matsunaga et al., Application of Differential Display to Identify Genes for Lung Cancer Detection in Peripheral Blood, Int. J. Cancer, 2002, vol. 100, pp. 592-599.

Mayringer et al., A critical comparison of frequently used methods for the analysis of tumor necrosis factor-alpha expression by human immune cells, Immunol Methods, 2000, vol. 235, Issue 1-2, pp. 33-40.

Mestres et al., A new method to assess drug sensitivity on breast tumor acute slices preparation, Annals of the New York Academy of Sciences; Cell Signaling World 2006 Conference, Jan. 25-28, 2006, pp. 460-469.

Mitsuhashi, Ex Vivo Simulation of Drug Action: Quantification of Drug-Induced mRNA as a Bridge Between Preclinical and Clinical Trials, Clinical Chemistry, 2007, vol. 53(1), pp. 148-149.

Mitsuhashi et al., Oligonucleotide probe design—a new approach, Nature, Feb. 24, 1994, vol. 367, pp. 759-761.

Mitsuhashi et al., Quantification of mRNA in Whole Blood by Assessing Recovery of RNA and Efficiency of cDNA Synthesis, Clinical Chemistry, 2006, vol. 52(4), pp. 634-642, pp. 634-642.

Mitsuhashi et al., Ex Vivo Simulation of the Action of Antileukemia Drugs by Measuring Apoptosis-Related mRNA in Blood, Clinical Chemistry, 2008, vol. 54(4), pp. 673-681, pp. 673-681.

Mitsuhashi et al., Quantification of Drug-Induced mRNA in Human Whole Blood ex vivo, Clinical Medicine: Blood Disorders, 2008, vol. 1, pp. 1-11.

Moronvalle-Halley et al., Evaluation of cultured, precision-cut rat liver slices as a model to study drug-induced liver apoptosis, Toxicology, Feb. 14, 2005, vol. 207, Issue 2, pp. 203-214.

Morrison et al., Quantification of low-copy transcripts by continuous SYBR Green I monitoring during amplification, Biotechniques, 1998, vol. 24, Issue 6, pp. 954-962.

Munger et al., Evidence for Inhibition of Growth Related to Compromised DNA Synthesis the Interaction of Daunorubicin with H-35 Rat Hepatoma, Cancer Research, May 1, 1988, vol. 48, pp. 2404-2411.

Naccarati et al., Sporadic colorectal cancer and individual susceptibility: A review of the association studies investigating the role of DNA repair genetic polymorphisms, Mutation Research, 2007, vol. 635, pp. 118-145.

Nave et al., In vitro metabolism of ciclesonide in human lung and liver precision-cut tissue slices, Biopharmaceutics & Drug Disposition, May 2006, vol. 27, Issue 4, pp. 197-207.

Oldenburg et al., Genetic susceptibility for breast cancer: How many more genes to be found?, Oncology Hematology, 2007, vol. 63, pp. 125-149.

Parrish et al., Culturing precision-cut human prostate slices as an in vitro model of prostate pathobiology, Cell Biology and Toxicology, May 1, 2002, vol. 18, Issue 3, pp. 205-219.

Paterson et al., Defective excision repair of y-ray-damaged DNA in human (ataxia telangiectasia) fibroblasts, Nature, Apr. 1, 1976, vol. 260, pp. 444-447.

Ranganathan, "Pharmacogenomics of tumor necrosis factor antagonists in rheumatoid arthritis," Pharmacogenomics, Ashley Publications, GB, Jul. 1, 2005, vol. 6(5), pp. 481-490, XP009086991, ISSN: 1462-2416.

Schimanski et al., "Effect of Chemokine Receptors CXCR4 and CCR7 on the Metastatic Behavior of Human Colorectal Cancer," Clinical Cancer Research, vol. 11, No. 5, Mar. 2005, pp. 1743-1750.

\* cited by examiner

ENHANCED FC RECEPTOR-MEDIATED TUMOR NECROSIS FACTOR SUPERFAMILY MRNA EXPRESSION IN PERIPHERAL BLOOD LEUKOCYTES IN PATIENTS WITH RHEUMATOID ARTHRITIS

BACKGROUND

1. Field

The disclosure relates to a method for predicting patient responsiveness to treatments for rheumatoid arthritis involving a tumor necrosis factor superfamily member or a cytokine, to a method of monitoring the effectiveness of such therapy, and to a method for screening compounds for use in the treatment of rheumatoid arthritis. The disclosure also relates to a method for monitoring the disease state in rheumatoid arthritis patients.

2. Description of the Related Art

Autoimmune disease is characterized by production of either antibodies that react with host cells or immune effector T cells that are autoreactive. Autoantibodies are frequently identified in certain types of autoimmune disease, such as anti-acetylcholine receptor antibodies in myasthenia gravis and anti-DNA antibodies in systemic lupus erythematosus. However, such autoantibodies are not seen in many types of autoimmune disease. Moreover, autoantibodies are often detected among healthy individuals, but such antibodies do not induce autoimmune disease. Thus, beside autoantibodies, additional yet-to-be identified mechanisms are evidently involved in the pathogenesis of autoimmune disease.

Once autoantibodies bind to the target host cells, the complement cascade is thought to be activated to form the C5-9 membrane attack complex on the target cell membranes, which leads to the death of host cells (see Esser, *Toxicology* 87, 229 (1994)). Byproduct chemotactic factors, such as C3a, C4a, or C5a recruit more leukocytes to the lesion (see Hugh, *Crit. Rev. Immunol.* 1, 321 (1981)). Recruited leukocytes or naturally present leukocytes at the lesion recognize antibody-bound cells (immune complexes) via Fc receptors ("FcR"). Once the FcR is cross-bridged by the immune complex, leukocytes release TNF-α (see Debets et al., *J. Immunol.* 141, 1197 (1988)), which binds to specific receptors present on the surface of host cells, and induces apoptosis or cell damage (see Micheau et al., *Cell* 114, 181 (2003)). Activated FcR also initiates the release of chemotactic cytokines to recruit different subsets of leukocytes to the lesion (see Chantry et al., *Eur. J. Immunol.* 19, 189 (1989)). This is an overall hypothesis of the molecular mechanism of FcR-related autoimmune disease.

Rheumatoid arthritis ("RA") is an immune disease involving inflammation of the gastrointestinal tract. Although it is well characterized clinically, its pathogenesis is poorly understood. RA is characterized by persistent inflammatory synovitis, usually involving peripheral joints in a symmetric distribution. This may lead to cartilage destruction, bone erosion, and changes in joint integrity. The cause of RA remains unknown, but it is strongly suspected that CD4+ T-cells play a role in the disease because of the predominance of such cells in the synovium, the increase in soluble IL-2 receptors (produced by activated T-cells) in the blood and serum of RA patients, and the noted amelioration of the disease by removal of T-cells. RA is associated with a buildup of TNF-α (also known as TNFSF-2) in the joints. TNF-α normally serves to mobilize white blood cells to fight infections and other invaders, causing inflammation in the affected area. A healthy body can rid itself of excess TNF-α, but the body of a patient with rheumatoid arthritis cannot. As a result, more and more white blood cells travel to the affected area. The build up of TNF-α, particularly in the rheumatoid joint, causes inflammation, pain and tissue damage.

IgG Fc receptors (FcγR) are known to react with immune complexes (ICs) (the combination of an epitope with an antibody directed against that epitope) to elicit various inflammatory reactions. ICs are frequently identified at joint lesions in patients with RA, although specific antigens have not been not fully characterized. ICs are also known to activate complement cascades to establish inflammation, as well as antibody-dependent cell mediated cytotoxicity (ADCC) by binding to the FcγR of various leukocytes. Locally infiltrating leukocytes have been collected from synovial fluids and studied previously. However, because these collections contain both newcomer and exhausted cells, the results have been difficult to interpret. Since peripheral blood leukocytes play a major role in the pathogenesis of RA when they migrate to disease sites, numerous experiments have been conducted to simulate such functions in vitro. Typically, mononuclear leukocytes are isolated, suspended in culture media, and incubated in a $CO_2$ incubator with various stimulants or effector cells. However, the conditions under which such assays are conducted do not approximate physiological conditions, due to a lack of communication among different cell populations, oxygen supply from erythrocytes, as well as complex interactions with plasma proteins and other components. Secondary reactions may occur during the lengthy incubation period. Moreover, due to labor-intensive techniques and substantial experiment-to-experiment variations, these in vitro tests have less application in diagnostic testing.

Treatment of RA focuses on pain relief, reduction of inflammation, protection of articular structures, maintenance of function, and control of systemic involvement. Options include: aspirin and other nonsteroidal anti-inflammatory drugs; antirheumatic drugs such as methotrexate, gold compounds, D-penicillamine, the antimalarials, and sulfasalazine; glucocorticoids; TNF-α neutralizing agents such as infliximab and etanercept; and immunosuppressive drugs such as azathioprine, leflunomide, cyclosporine, and cyclophosphamide. Because the choice of therapeutic options depends on an assessment of the disease state in RA patients, it would be desirable to develop new methods of evaluating the disease state and monitoring the progression of the disease.

DETAILED DESCRIPTION OF THE PREFERRED EMBODIMENTS

The present disclosure relates to the use of differential mRNA transcription patterns in leukocytes in response to specific cellular stimuli in assessing whether RA patients are good candidates for specific therapies. The present disclosure also relates to the use of such differential transcription patterns in assessing whether therapy administered to an RA patient is effective. The present disclosure also relates to the use of such differential transcription patterns in screening candidate agents for use in treating RA. The present disclosure also relates to the use of such differential transcription patterns in evaluating the state of RA in patients over time and monitoring the progression of the disease.

As described above, the pathology of RA may be related to the interaction between FcγR in the immune cells of an RA patient and the IC. In order to further assess this possibility, heat aggregated IgG (HAG, a classic model of the IC) was used to stimulate FcγR in human whole blood in both healthy adult controls and patients with RA. Other stimuli that can be used include phorbol myristate acetate (PMA), phytohemagglutinin (PHA), wheat germ agglutinin (WGA), concanavalin-A (ConA), lipopolysaccharides (LPS), jacalin, fucoidan, heat-aggregated IgE, heat-aggregated IgA, and heat-aggregated IgM.

HAG was added directly into heparinized whole blood, and the changes in the mRNA level of various members of the tumor necrosis factor superfamily (TNFSF) were assessed. Although multiple FcγRs exist, such as FcγRI, IIa, IIb, and III (GeneBank UniGene database), HAG acts as a universal stimulus that can react with all FcR subtypes. The changes in the mRNA level of members of the TNFSF mRNA (see, for example, the GeneBank UniGene database) resulting from the stimulus with HAG were quantified.

As stated, FcγR-mediated functions consist of four subclasses of the Fc portions of IgG (IgG1-4), multiple classes of FcγR (FcγRIa-c, FcγRIIa-c, and FcγRIIIa-b), different subsets of FcγR-bearing leukocytes, and various downstream intracellular signalling cascades. Moreover, these proteins have multiple transcript variants and various genetic polymorphisms. Altered functions of FcγR in disease states may happen at any level. However, it may be impractical to characterize each factor in each individual. The present disclosure contemplates use of whole blood (with its attendant ex vivo conditions) as a screening tool to identify individuals who would benefit from various downstream assays, such as individual cell analysis, genotyping of various genes, and variation of intracellular signalling cascades. All of the tumor necrosis factor superfamily (TNFSF) members were screened in this way, as IC is known to induce TNFSF-2 (=TNF-α) and TNFSF-15 (=TL1A) mRNA.

The method employed was as follows. Nucleotide sequences for various TNFSF genes were retrieved from the UniGene database in the GenBank. PCR primers for each gene were designed by Primer Express (Applied Biosystem, Foster City, Calif.) and HYBsimulator (RNAture, Irvine, Calif.) (see Mitsuhashi et al., Nature 367, 759 (1994); Hyndman et al., BioTechniques 20, 1090 (1996)). The sequences are summarized in Table I below. Oligonucleotides were synthesized by IDT (Coralville, Iowa), Tsukuba Oligo Service (Tsukuba, Japan), Nippon EGT (Toyama, Japan), and Hokkaido System Science (Sapporo, Japan).

TABLE 1

Primer Sequences

| Target mRNA | Forward(3'-5') | SEQ ID NO | Reverse (3'-5') | SEQ ID NO |
|---|---|---|---|---|
| TNFSF-1 | CAGCTATCCACCCACACAGATG | 1 | CGAAGGCTCCAAAGAAGACAGT | 2 |
| TNFSF-2 | CGAAGGCTCCAAAGAAGACAGT | 3 | CAGGGCAATGATCCCAAAGT | 4 |
| TNFSF-3 | AGGGTGTACGTCAACATCAGTCA | 5 | CACGGCCCCAAAGAAGGT | 6 |
| TNFSF-4 | GCCCTCTTCCAACTGAAGAA | 7 | GGTATTGTCAGTGGTCACATTCAAG | 8 |
| TNFSF-5 | CCACAGTTCCGCCAAACCT | 9 | CACCTGGTTGCAATTCAAATACTC | 10 |
| TNFSF-6 | TGGCAGCATCTTCACTTCTAAATG | 11 | GAAATGAGTCCCCAAAACATCTCT | 12 |
| TNFSF-7 | CACACTCTGCACCAACCTCACT | 13 | TGCACTCCAAAGAAGGTCTCATC | 14 |
| TNFSF-8 | ACCACCATATCAGTCAATGTGGAT | 15 | GAAGATGGACAACACATTCTCAAGA | 16 |
| TNFSF-9 | AGCTACAAAGAGGACACGAAGGA | 17 | CGCAGCTCTAGTTGAAAGAAGACA | 18 |
| TNFSF-12 | TACTGTCAGGTGCACTTTGATGAG | 19 | CGCAGTGGCTGAGAATTCCT | 20 |
| TNFSF-13 | ATATGGTGTCCGAATCCAGGAT | 21 | CCTGACCCATGGTGAAAGTCA | 22 |
| TNFSF-13B | ATGCCTGAAACACTACCCAATAATT | 23 | GCAAGTTGGAGTTCATCTCCTTCT | 24 |
| TNFSF-14 | CGTCCGTGTGCTGGATGA | 25 | CATGAAAGCCCCGAAGTAAGAC | 26 |
| TNFSF-15 | TGCGAAGTAGGTAGCAACTGGTT | 27 | CCATTAGCTTGTCCCCTTCTTG | 28 |

Heat aggregated IgG (HAG) was prepared by heating 20 mg/mL human IgG (Sigma, St. Louis) in PBS at 63° C. for 15 min (see Ostreiko et al., Immunol. Lett. 15, 311 (1987)). In 8-well strip microtubes, 1.4 μl of HAG or control (phosphate buffered saline) were added, and stored at −20° C. until use. Seventy μl of fresh heparinized whole blood (which was kept at 4° C. until stimulation with IC) was added into each well in triplicate, and incubated at 37° C. for 4 hours with the cap closed. The blood samples were treated on the same day as the blood draw. After treatment, each blood sample was stored frozen at −80° C. until use.

The mRNA and cDNA were prepared from whole blood following the method set forth in Mitsuhashi et al., Clin. Chem. 52, 634 (2006). The method disclosed in U.S. patent application Ser. No. 10/796,298, which is incorporated here by reference, may also be employed. In brief, 50 µl of whole blood was transferred to 96-well filterplates in order to trap the leukocytes therein; these filterplates were placed over collection plates, and 150 µl 5 mM Tris, pH 7.4, was applied. Following centrifugation at 120×g for 1 min at 4° C., 50 µl of blood sample was applied to each well and immediately centrifuged at 120×g for 2 min at 4° C., followed by washing of each well with 300 µl PBS once with centrifugation at 2000×g for 5 min at 4° C. Then, 60 µl stock lysis buffer, supplemented with 1% 2-mercaptethanol (Bio Rad, Hercules, Calif., USA), 0.5 mg/ml proteinase K (Pierce, Rockford, Ill., USA), 0.1 mg/ml salmon sperm DNA (5 Prime Eppendorf/Brinkmann, Westbury, N.Y., USA), 0.1 mg/ml E. coli tRNA (Sigma), a cocktail of 10 mM each of specific reverse primers, and standard RNA34 oligonucleotides, were applied to the filterplates, followed by incubation at 37° C. for 10 min The filterplates were then placed over oligo(dT)-immobilized microplates (GenePlate, RNAture) (see Mitsuhashi et al., Nature 357, 519 (1992); Hamaguchi et al., Clin. Chem. 44, 2256 (1998) (both incorporated herein by reference)), and centrifuged at 2000×g for 5 min at 4° C. Following overnight storage at 4° C., the microplates were washed with 100 µl plain lysis buffer three times, followed by 150 µl wash buffer (0.5 M NaCl, 10 mM Tris, pH 7.4, 1 mM EDTA) three times at 4° C. The cDNA was directly synthesized in 30 µl solutions in each well by adding buffer containing 1×RT-buffer, 1.25 mM each of dNTP, 4 units rRNasin, and 80 units of MMLV reverse transcriptase (Promega) (without primers), and incubating at 37° C. for 2 hours. The specific primer-primed cDNA existed in solution, and oligo(dT)-primed cDNA stayed immobilized in the microplate (see Hugh, Crit. Rev. Immunol. 1, 321 (1981)). For SYBR Green PCR (see Morrison et al., Biotechniques 24, 954 (1998) (incorporated herein by reference)), cDNA was diluted 4-fold in water, and 4 µl of cDNA solution was directly transferred to 384-well PCR plates, to which 5 µl iTaq SYBR master mix (BioRad, Hercules, Calif.) and 1 µl oligonucleotide cocktail (15 µM each of forward and reverse primer) were applied, and PCR was conducted in PRISM 7900HT (ABI), with one cycle of 95° C. for 10 mM followed by 45 cycles of 95° C. for 30 sec and 60° C. for 1 mM TaqMan PCR could also be employed; in such a case, the cDNA solution is directly transferred to 384-well PCR plates, to which 5 µl of TaqMan universal master mix (ABI) and 1 µl oligonucleotide cocktail (15 µM each of forward and reverse primer, and 3-6 µM TaqMan probe) are applied, and PCR is conducted in PRISM 7900HT (ABI), with one cycle of 95° C. for 10 min followed by 45 cycles of 95° C. for 30 sec, 55° C. for 30 sec, and 60-65° C. for 1 min. Each gene was amplified individually.

The 1× RT buffer was used as a negative control to confirm that no primer dimer was generated under SYBR Green PCR conditions. Moreover, the melting curve was analyzed in each case to confirm that PCR signals were derived from a single PCR product. The cycle threshold (Ct), which was the number of PCR cycles required to generate certain amounts of PCR products (fluorescence), was determined by analytical software (SDS, ABI). The Ct values of HAG-treated triplicate samples were reduced by the mean Ct values of PBS controls individually to calculate $\Delta Ct$, and the fold increase for stimulated samples compared to unstimulated samples (hereinafter simply referred to as the "fold increase") was calculated as $2^{(-\Delta Ct)}$, by assuming that the efficiency of each PCR cycle was 100%.

Figure 1:
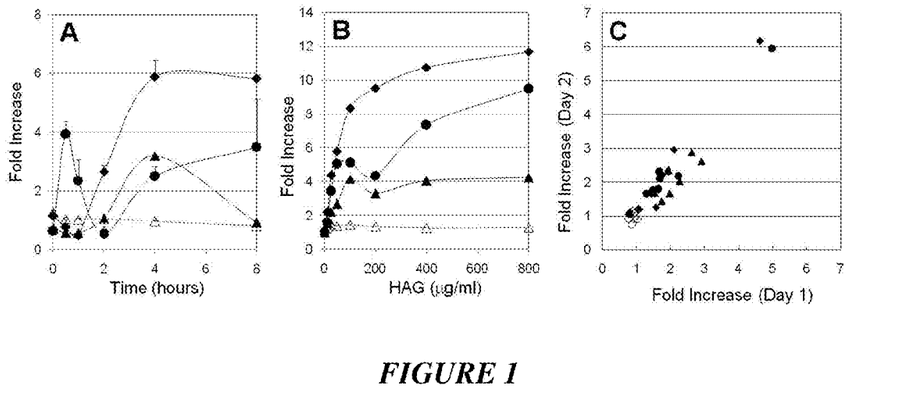
FIGS. 1A-1C show the results of quantification of FcγR-mediated gene expression of various TNFSF mRNAs in human leukocytes in peripheral whole blood.

FIGS. 1A-C show FcγR-mediated mRNA expression in peripheral blood leukocytes. Each data point represents the mean±standard deviation (FIG. 1A) or mean (FIGS. 1B, 1C) from triplicate aliquots of whole blood.

FIG. 1A shows the results of an analysis of the kinetics of the expression. Triplicate aliquots of 70 µl each of heparinized whole blood were mixed with PBS or 200 µg/ml of heat aggregated IgG (HAG) and incubated at 37° C. for 0-8 hours. TNFSF-2 (=TNF-α, •), TNFSF-8 (▲), TNFSF-15 (=TL1A, ♦), and β-actin (Δ) mRNA were then quantified and the fold increase (y-axis) was calculated as described above. As shown in FIG. 1A, the induction of TNFSF-2 was very rapid with a peak around 30 min followed by a large sustained peak around 4 hours. In contrast to TNFSF-2, TNFSF-8 (FIG. 1A, ▲) and TNFSF-15 (=TL1A) (FIG. 1A, ♦) increased slowly with a peak around 4 hours. A housekeeping gene (β-actin) was not induced during incubation for 8 hours with HAG (FIG. 1A, Δ). HAG incubation was accordingly fixed at 4 hours to analyze TNFSF-2, -8 and -15 mRNA. This short incubation (4 hours) is one of the advantages of an mRNA-based assay, because protein detection requires at least overnight incubation to identify drug-induced changes.

FIG. 1B shows the dose response. Heparinized whole blood was incubated with 0-800 µg/ml HAG at 37° C. for 4 hours, then various mRNAs were quantified (each symbol is defined as in FIG. 1A). HAG-induced TNFSF-2, TNFSF-8, and TNFSF-15 were confirmed from 10 µg/ml of HAG in a dose dependent manner and saturated at 100-200 µg/ml, whereas β-actin was unchanged.

FIG. 1C shows the results obtained when blood was withdrawn from the same individuals twice within 1 week, and HAG-induced TNFSF-2 (●), TNFSF-8 (▲), TNFSF-15 (♦) mRNA and an external control mRNA (synthetic RNA34) (○) were quantified. As shown in FIG. 1C, the induction was reproducible and the $r^2$ value between Day 1 and Day 2 among 8 healthy individuals were 0.927 (n=32, p<0.001) (FIG. 1C). The fold increase of external synthetic RNA spiked into lysis buffer (RNA34, FIG. 1C, ○) was always less than 1.5, suggesting that the assay was performed appropriately in each experiment.

Although the actual blood volume used for mRNA analysis was 50 µl, the assay used 70 µl of whole blood per reaction (20 µl is a reserve during the transfer from 8-well strips to filterplates). Thus, each test consumed as little as 420 µl (=70 µl/well×2 (HAG and PBS)×3 (triplicate)) of whole blood. From 50 µl of whole blood/well, 30 different mRNAs were quantified by RT-PCR (30 µl cDNA plus 90 µl water (1:4 dilution), 4 µl cDNA/PCR). Even from 1:4 dilution of cDNA, measurement of various TNFSF mRNAs was achieved. Unlike serum-based tests, where serum volume is unpredictable due to the variation of hematocrit among individuals, whole blood is easy to manipulate.

Table 2 shows the results of an analysis of the FcR-mediated gene expression of TNFSF mRNA in human leukocytes in peripheral whole blood. The results shown are expressed as a percentage of "responder" subjects, defined as those subjects that exhibit a fold increase of greater than 2 in response to HAG stimulation. The $\chi^2$ test was used to compare the incidence of positive responses between healthy subjects and RA patients for each TNFSF mRNA. Since there were two populations (positive and negative responses), the t-test was only applied to the subjects with a fold increase of greater than 2.

TABLE 2

Immune complex-induced TNFSF mRNA expression.

| TNFSF | Control No. positive*/n | % | RA No. positive/n | % | p value |
|---|---|---|---|---|---|
| TNFSF-1 | 7/39 | 18 | 2/16 | 13 | n.s. |
| TNFSF-2 | 15/40 | 38 | 30/59 | 51 | n.s. |
| TNFSF-3 | 2/40 | 5 | 4/60 | 7 | n.s. |
| TNFSF-4 | 1/40 | 3 | 4/57 | 7 | n.s. |
| TNFSF-5 | 0/40 | 0 | 0/61 | 0 | n.s. |
| TNFSF-6 | 1/40 | 3 | 7/61 | 11 | n.s. |
| TNFSF-7 | 8/40 | 20 | 6/58 | 10 | n.s. |
| TNFSF-8 | 25/40 | 63 | 25/61 | 41 | n.s. |
| TNFSF-9 | 7/36 | 19 | 7/52 | 13 | n.s. |
| TNFSF-12 | 0/40 | 0 | 1/26 | 4 | n.s. |
| TNFSF-13 | 0/40 | 0 | 0/26 | 0 | n.s. |
| TNFSF-13B | 1/40 | 3 | 0/24 | 0 | n.s. |
| TNFSF-14 | 19/40 | 48 | 20/57 | 35 | n.s. |
| TNFSF-15 | 38/38 | 100 | 58/61 | 95 | n.s. |

*Fold increase > 2.0

As shown in Table 2, HAG induced TNFSF-15 (=TL1A) mRNA (fold increase >2) in all cases of healthy donors, and 59 out of 61 RA patients. These results replicated, under ex vivo conditions, recently published reports (see Prehn et al., *The T cell costimulator TL1A is induced by FcgammaR signaling in human monocytes and dendritic cells*, J. Immunol. 178, 4033 (2007); Cassatella et al., *Soluble TNF-like cytokine (TL1A) production by immune complexes stimulated monocytes in rheumatoid arthritis*, J. Immunol. 178, 7325 (2007) (both incorporated herein by reference)). HAG is also known to induce TNFSF-2 (=TNF-α) mRNA (see Satoh et al., *Endogenous production of TNF in mice with immune complex as a primer*, J. Biol. Response Mod. 5, 140 (1986); Chouchakova et al., *Fc gamma RIII-mediated production of TNF-alpha induces immune complex alveolitis independently of CXC chemokine generation*, J. Immunol. 166, 5193 (2001) (both incorporated herein by reference)). However, as shown in Table 2, TNFSF-2 was not found to be induced in all individuals, and more than half of the subjects failed to respond. Furthermore, HAG stimulation induced TNFSF-8 (=CD153, CD30 ligand) and TNFSF-14 (=LIGHT) mRNA in more than ⅓ of controls and RA patients, and TNFSF-1 (=lymphotoxin α, LTA), TNFSF-3 (=lymphotoxin β, LTB), TNFSF-4 (=CD252, CD134 ligand), TNFSF-6 (=Fas ligand), TNFSF-7 (=CD70, CD27 ligand), and TNFSF-9 in some cases, whereas TNFSF-5 (=CD154, CD40 ligand), TNFSF-12 (=TWEAK), TNFSF-13 (=CD256), and TNFSF-13B (=CD257) showed little or no induction. This individual-to-individual variation, or the presence of responders and non-responders at 4 hours from the start of stimulation was meaningful because, as shown in FIGS. 1A and 1B, saturation was achieved at incubation for 4 hours with 200 μg/ml HAG. This ex vivo assay is expected to be useful as a screening platform for various downstream assays.

A test for rheumatoid factor (RF) (either Type 2 (monoclonal IgM to polyclonal IgG) or 3 (polyclonal IgM to polyclonal IgG) cryoglobulin) is a standard diagnostic method in cases of suspected RA. The results of TNFSF-2, TNFSF-8, and TNFSF-15 induction resulting from HAG stimulation were broken out by RF levels to look for correlations. The results are shown in FIGS. 2A-2C. HAG-induced TNFSF-2 (A), TNFSF-8 (B), and TNFSF-15 (C) mRNA were quantified from 40 healthy adult volunteers (control), and 61 RA patients with RF<30, 30-100, and >100 IU/ml, respectively. Because two populations were observed (responders with fold increase >2, and non-responders), the t-test was only applied to the responder population. Analysis by $\chi^2$ test revealed no significant difference among these four groups.

Figure 2:
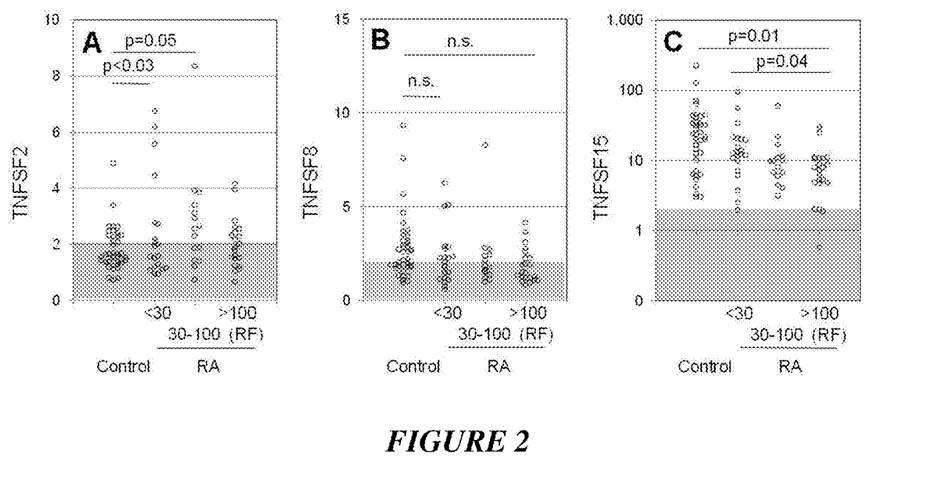
FIGS. 2A-2C show the fold increases in various TNFSF mRNA levels induced by heat aggregated IgG (HAG) stimulation in the whole blood of rheumatoid arthritis patients and control patients as compared to unstimulated whole blood from said patients.

As shown in FIG. 2, classification of RA patients by amount of RF revealed significant differences in TNFSF induction. As shown in FIG. 2C, the fold increase of TNFSF-15 in RA patients with RF>100 IU/ml was significantly less than that of control (p=0.01) and RA patients with RF<30 IU/ml (p=0.04), respectively. This probably results from the fact that RF is a native form of IC and was present in the whole blood when HAG was added ex vivo. The majority of RA patients maintained the response to HAG stimulation. This indicates that circulating leukocytes in peripheral blood of RA patients are still capable of activating an IC despite a long period of exposure to RF. Reduced TNFSF-15 responses shown in RA patients with high RF may indicate that TNFSF-15 receptor function in peripheral blood leukocytes is somehow down-regulated.

In view of the activation of FcγR by RF, an assessment was made of whether the baseline levels of TNFSF-15 mRNA are elevated by the continuous exposure to RF. The results were measured in terms of Ct by calculating the relative expression of TNFSF-15 over TNFSF-5, -13, and -13B, because these three TNFSF mRNAs were not induced by HAG, as shown in Table 2. However, the basal levels of TNFSF-15 in RA patients were not found to be significantly different from control subjects in all three calculations.

Figure 3:
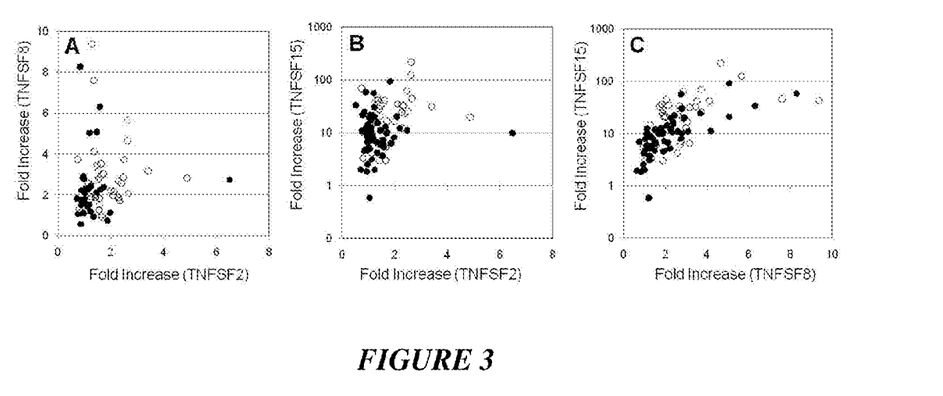
FIGS. 3A-3C show comparative fold increases in various TNFSF mRNA levels induced by heat aggregated IgG (HAG) stimulation in the whole blood of rheumatoid arthritis patients and control patients as compared to unstimulated whole blood from said patients.

FIG. 3 shows the results obtained when the results shown in FIG. 2 were transformed to an x-y graph by comparing TNFSF-2 and -8 (A), TNFSF-2 and -15 (B), and TNFSF-8 and -15 (C), with control (○) and RA (●), respectively. As shown in FIG. 3C, the fold increase of TNFSF-15 was well correlated with that of TNFSF-8 in both RA (●) and healthy subjects (○) with $r^2$ values of 0.48 (n=61, p<0.001) and 0.27 (n=38, p<0.001), respectively. However, because the fold increase of TNFSF-8 was lower and the population of positive responders was smaller than that of TNFSF-15, a significant difference was not observed for TNFSF-8 between control and RA, even when RA patients were classified by the amount of RF (FIG. 2B). However, in contrast to TNFSF-15, the fold increase of TNFSF-2 in RA patients with RF<30 and <100 was significantly (p<0.03, 0.05) higher than that of healthy subjects, as shown in FIG. 2A. The fold increase of TNFSF-2 was not correlated to that of TNFSF-8 (FIG. 3A) ($r^2$=0.03 and 0.02 for control and RA, respectively) and TNFSF-15 (FIG. 3B) ($r^2$=0.11 and 0.003 for control and RA, respectively), suggesting that TNFSF-2 and TNFSF-8/-15 are derived from distinct pathways. This was further confirmed by the evidence shown in FIG. 1A, where the kinetics between TNFSF-2 and TNFSF-8/-15 were different.

TNFSF-2 (=TNF-α) is one of the inflammatory cytokines involved in the pathogenesis of RA, and is present in synovial fluid in RA (see Saxne et al., *Detection of tumor necrosis factor alpha but not tumor necrosis factor beta in rheumatoid arthritis synovial fluid and serum*, Arthritis Rheum. 31, 1041 (1988) (incorporated herein by reference)). It has been shown by in situ hybridization that TNF-α transcripts were present in synovial tissue macrophages (see MacNaul et al., *Analysis of IL-1 and TNF-alpha gene expression in human rheumatoid synoviocytes and normal monocytes by in situ hybridization*, J. Immunol. 145, 4154 (1990) (incorporated herein by reference)). Moreover, anti-TNF-α monoclonal antibodies (infliximab, Remicade) and soluble TNF receptors (etanercept, Enbrel) which block the action of TNF-α have demonstrated clinical efficacy in patients with RA (see Weaver, *The impact of new biologicals in the treatment of rheumatoid arthritis*, Rheumatology (Oxford) 43 Suppl. 3:iii17-iii23 (2004) (incorporated herein by reference)). Thus, the elevated HAG-induced TNF-α induction shown in RA patients in our ex vivo assay is quite reasonable. mRNA induction does not, of course, always correspond to protein synthesis and subsequent biological and clinical outcomes due to altered splicing, post-translational modification, and co-activation of inhibitory cascades. However, this ex vivo simulation will be effective as a starting point screening tool for various downstream molecular assays, such as genetic polymorphisms of receptors and associated proteins.

We also compared patients' clinical characteristics between responders (fold increase >=2) and non-responders (fold increase <2) of HAG-induced TNFSF-2 mRNA. The results are shown in Table 3.

TABLE 3

Characteristics of responders and non-responders on HAG-induced TNFSF-2

| | | HAG-induced TNFSF-2 | | |
|---|---|---|---|---|
| | | FI* >= 2 | FI* < 2 | p value |
| RF < 30 | N | 9 | 11 | |
| | Age (years) | 54.6 ± 12.1 | 66.5 ± 11.8 | 0.04 |
| | Male:Female | 0:9 | 1:10 | 0.35** |
| | Duration (years) | 2.4 ± 1.1 | 6.2 ± 7.5 | 0.2 |
| | CRP | 0.1 ± 0.1 | 0.5 ± 0.8 | 0.17 |
| | No. swelling/joint | 2.9 ± 3.8 | 3.7 ± 4.2 | 0.7 |
| | No. pain/joint | 1.7 ± 3.1 | 0.7 ± 1.6 | 0.4 |
| | Treatment with Remicade/Enbrel | 3 | 1 | 0.2** |
| RF 30-100 | N | 9 | 6 | |
| | Age (years) | 64.2 ± 6.0 | 62.0 ± 18.3 | 0.74 |
| | Male:Female | 2:7 | 1:5 | 0.79** |
| | Duration (years) | 8.9 ± 7.8 | 6.7 ± 4.6 | 0.5 |
| | CRP | 1.0 ± 1.8 | 0.2 ± 0.3 | 0.28 |
| | No. swelling/joint | 1.9 ± 2.2 | 2.0 ± 3.2 | 0.9 |
| | No. pain/joint | 0.8 ± 2.1 | 0.5 ± 1.2 | 0.8 |
| | Treatment with Remicade/Enbrel | 2 | 0 | 0.2** |
| RF > 100 | N | 10 | 11 | |
| | Age (years) | 56.6 ± 11.5 | 54.5 ± 16.5 | 0.75 |
| | Male:Female | 2:8 | 1:10 | 0.4** |
| | Duration (years) | 9.0 ± 17 | 5.6 ± 2.9 | 0.5 |
| | CRP | 1.4 ± 2.2 | 1.6 ± 2.6 | 0.9 |
| | No. swelling/joint | 5.0 ± 7.3 | 8.3 ± 7.3 | 0.3 |
| | No. pain/joint | 2.9 ± 5.1 | 5.6 ± 5.3 | 0.2 |
| | Treatment with Remicade/Enbrel | 2 | 0 | 0.1** |
| All | N | 28 | 28 | |
| | Age (years) | 58.4 ± 1.07 | 60.9 ± 15.6 | 0.5 |
| | Male:Female | 4:24 | 3:25 | 0.7** |
| | Duration (years) | 6.9 ± 11.0 | 6.1 ± 5.3 | 0.7 |
| | CRP | 0.9 ± 1.7 | 0.9 ± 1.7 | 0.9 |
| | No. swelling/joint | 3.4 ± 5.2 | 5.2 ± 6.0 | 0.3 |
| | No. pain/joint | 1.9 ± 3.8 | 2.7 ± 4.3 | 0.5 |
| | Treatment with Remicade/Enbrel | 7 | 1 | 0.02** |

*FI: fold increase,
**$\chi^2$ test

As shown in Table 3, the responder population in the RF<30 IU/ml group was significantly (p=0.04) younger than that of non-responders. Other clinical parameters, such as age, gender, disease duration, CRP, number of swelling joints, and number of tender joints were not significantly different between responders and non-responders in all RF groups (Table 3). Interestingly, when all patients were combined, the number of patients treated with biological agents such as an anti-TNF-α monoclonal antibody or a soluble TNF receptor were significantly (p=0.02) higher in the responder population than in the non-responder population (Table 3). Use of these anti-TNF-α agents may enhance FcγR-mediated TNF-α function through an unidentified negative feedback mechanism, or such patients may be good candidates for biological therapy. RA patients that show response in HAG-induced TNF-α mRNA are more likely to have a significant TNF-α participation in the RA pathology, and therefore are more likely to be good candidates for these biological agents. Since biological drugs are very expensive, not effective in all patients, and occasionally show undesirable side effects, the identification of patients likely to respond to these drugs will have clinical utility as personalized medicine.

Cytotoxic assays have generally been used to study actual cell death resulting from the activity of the immune system, such as that which is believed to occur in RA. Cytotoxic assays are generally conducted by incubating $^{51}$Cr-loaded target cells with effector cells at various ratios, and quantifying the amounts of $^{51}$Cr radioactivity released from the dead or damaged cells (see Dunkley et al., *J. Immunol. Methods* 6, 39 (1974)). Radioactive materials have been replaced with non-radioactive materials, such as fluorometric materials, in some cases (see Kruger-Krasagakes et al., *J. Immunol. Methods* 156, 1 (1992)), but the basic principle is unchanged. The results of cytotoxic assays are thus reflective of actual cell death.

However, cytotoxic assays are performed under non-physiological experimental conditions, and complex cell-to-cell and cell-to-plasma interactions are difficult to assess in the course of such studies. Furthermore, cytotoxic assays do not indicate which TNFSF member is responsible for cell death. Once effector cells recognize the target cells, the effector cells' function is not only to kill the target, but also to recruit other effector cells, because a single effector cell is not enough to kill many target cells. This recruitment function is thought to be represented by the release of chemotactic factors. The identity of such chemotactic factors released by effector cells would not be revealed by classic cytotoxic assays. The assay system set forth in this disclosure is, however, capable of identifying many classes of gene expression in effector cells simultaneously.

The use of whole blood is preferable to using isolated leukocytes in culture media, because the former is more physiological than the latter, and whole populations of leukocytes can be screened. Longer incubation of whole blood may produce additional artifacts. Thus, the ideal way is to identify early signals of killer and recruitment signals in whole blood during a short period of incubation by switching in vitro to ex vivo. The transcription of mRNA is an earlier event than either protein synthesis or the final biological outcomes. Thus, mRNA is a logical target.

Since the present method uses whole blood, it may be used as a diagnostic test for RA to evaluate possible responsiveness to TNFSF-inactivating therapy, and to monitor the therapeutic response. Specifically, in a preferred embodiment of a method for determining whether a human having RA is likely to respond to a therapy targeting an mRNA transcribed in response to T-cell stimulation, whole blood is obtained from an RA patient and samples of the blood are subjected to HAG stimulation and optionally to control stimulation (PBS), as described above. The amount of TNFSF-2, TNFSF-8, or TNFSF-15 mRNA may be measured in the samples as described above. An RA patient having a significantly elevated level of one or more of these mRNAs after stimulation with HAG (as indicated, for example, by a fold increase of greater than 2) is a good candidate for therapy targeting these mRNAs.

Furthermore, in a preferred embodiment of a method of evaluating the effectiveness of RA treatment targeting one or more of the TNFSF-2, TNFSF-8, or TNFSF-15 mRNAs in a patient, a first ratio of the amount of the mRNA in whole blood after HAG stimulation to the amount after control stimulation is obtained prior to the initiation of the treatment. A second ratio of the amount of the mRNA in whole blood after HAG stimulation to the amount after control stimulation is obtained after the initiation of the treatment. A significant difference in the ratios, such as where the first ratio is larger than the second ratio, can indicate the effectiveness of the therapy. Such therapies could include, for example, the administration of infliximab or etanercept.

Importantly, this ex vivo method can be used for the screening of compounds which inhibit anti-FcR-mediated expression of one or more of the TNFSF-2, TNFSF-8, or TNFSF-15 mRNAs, and particularly TNFSF-2, which is known to participate in disease pathology. Such compounds will be interesting drug targets, because these new drug candidates will block mRNA production in leukocytes at the transcription level. This will provide a new strategy for drug development against RA.

In an embodiment of a method of screening drug compounds using the disclosed system and thereby identifying a putative agent for treating RA, whole blood is obtained from RA patients that are responders, wherein responders are individuals whose leukocytes exhibit at least a 2-fold increase in the level of an RA-associated mRNA when exposed to a T-cell stimulation such as HAG. A first ratio of the amount of the mRNA in whole blood of the subjects after HAG stimulation to the amount after control stimulation is calculated. Further whole blood samples from the subjects are exposed in vitro to the drug compound, and then differentially stimulated as described above. A second ratio of the amount of the mRNA in whole blood after HAG stimulation to the amount after control stimulation of these exposed samples is then calculated. A significant difference in the two ratios, such as where the first ratio is larger than the second ratio, can indicate that the drug compound is a candidate for further investigation as a potential therapeutic for RA.

Additionally, in a preferred embodiment of a method of monitoring the state of the disease in a RA patient by measuring levels of one or more of TNFSF-2, TNFSF-8, or TNFSF-15 mRNAs in samples comprising leukocytes obtained from the patient, a first ratio of the amount of the mRNA in whole blood after T-cell stimulus using heat-aggregated IgG antibody or another stimulus in vitro to the amount after control stimulation in vitro is obtained at a first time. At a second time subsequent to the first time, a second ratio of the amount of the mRNA in whole blood after the T-cell stimulus in vitro to the amount after control stimulation in vitro is obtained. A significant difference in the ratios can indicate a change in the disease state. For example, when the second ratio is larger than the first, this can indicate disease progression, while a larger first ratio can indicate that the disease has regressed.

What is claimed is:

1. A method of determining whether a patient having rheumatoid arthritis is likely to respond to anti-TNF therapy, comprising:
    stimulating the Fc receptors of leukocytes in vitro in a first sample from said patient for a period of four hours or longer;
    measuring the amount of an mRNA encoding a tumor necrosis factor superfamily member 2 ("TNFSF-2") protein in the first sample after the stimulation;
    exposing leukocytes in vitro in a second sample to a control stimulus;
    measuring the amount of said mRNA in the second sample;
    determining a ratio of the amount of mRNA in the first sample to the amount of mRNA in the second sample; and
    determining that the patient is likely to respond to the therapy if the ratio is about 2:1 or greater.

2. The method of claim 1, wherein stimulating leukocytes in the first sample comprises intermixing heat-aggregated human IgG with the first sample.

3. The method of claim 1, wherein at least one of the first and second samples comprises whole blood.

4. The method of claim 1, wherein the control stimulus is phosphate-buffered saline.

5. The method of claim 1, wherein the therapy comprises administration of an agent selected from the group consisting of infliximab and etanercept.

* * * * *

SEQUENCE LISTING

```
<160> NUMBER OF SEQ ID NOS: 28

<210> SEQ ID NO 1
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: TNFSF-1 Forward Primer

<400> SEQUENCE: 1
cagctatcca cccacacaga tg                                              22

<210> SEQ ID NO 2
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: TNFSF-1 Reverse Primer

<400> SEQUENCE: 2
cgaaggctcc aaagaagaca gt                                              22

<210> SEQ ID NO 3
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: TNFSF-2 Forward Primer

<400> SEQUENCE: 3
cgaaggctcc aaagaagaca gt                                              22
```

<210> SEQ ID NO 4
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: TNFSF-2 Reverse Primer

<400> SEQUENCE: 4
cagggcaatg atcccaaagt                                          20

<210> SEQ ID NO 5
<211> LENGTH: 23
<212> TYPE: DNA
<213> ORGANISM: Homo sapiens
<220> FEATURE:
<221> NAME/KEY: misc_feature
<222> LOCATION: (1)..(23)
<223> OTHER INFORMATION: TNFSF-3 Forward Primer

<400> SEQUENCE: 5
agggtgtacg tcaacatcag tca                                      23

<210> SEQ ID NO 6
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: TNFSF-3 Reverse Primer

<400> SEQUENCE: 6
cacggcccca aagaaggt                                            18

<210> SEQ ID NO 7
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: TNFSF-4 Forward Primer

<400> SEQUENCE: 7
gcccctcttc caactgaaga a                                        21

<210> SEQ ID NO 8
<211> LENGTH: 25
<212> TYPE: DNA
<213> ORGANISM: Homo sapiens
<220> FEATURE:
<221> NAME/KEY: misc_feature
<222> LOCATION: (1)..(25)
<223> OTHER INFORMATION: TNFSF-4 Reverse Primer

<400> SEQUENCE: 8
ggtattgtca gtggtcacat tcaag                                    25

<210> SEQ ID NO 9
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: TNFSF-5 Forward Primer

<400> SEQUENCE: 9

```
ccacagttcc gccaaacct                                              19
```

<210> SEQ ID NO 10
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: TNFSF-5 Reverse Primer

<400> SEQUENCE: 10

```
cacctggttg caattcaaat actc                                        24
```

<210> SEQ ID NO 11
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: TNFSF-6 Forward Primer

<400> SEQUENCE: 11

```
tggcagcatc ttcacttcta aatg                                        24
```

<210> SEQ ID NO 12
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: TNFSF-6 Reverse Primer

<400> SEQUENCE: 12

```
gaaatgagtc cccaaaacat ctct                                        24
```

<210> SEQ ID NO 13
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: TNFSF-7 Forward Primer

<400> SEQUENCE: 13

```
cacactctgc accaacctca ct                                          22
```

<210> SEQ ID NO 14
<211> LENGTH: 23
<212> TYPE: DNA
<213> ORGANISM: Homo sapiens
<220> FEATURE:
<221> NAME/KEY: misc_feature
<222> LOCATION: (1)..(23)
<223> OTHER INFORMATION: TNFSF-7 Reverse Primer

<400> SEQUENCE: 14

```
tgcactccaa agaaggtctc atc                                         23
```

<210> SEQ ID NO 15
<211> LENGTH: 24
<212> TYPE: DNA
<213> ORGANISM: Homo sapiens
<220> FEATURE:
<221> NAME/KEY: misc_feature

```
<222> LOCATION: (1)..(24)
<223> OTHER INFORMATION: TNFSF-8 Forward Primer

<400> SEQUENCE: 15
accaccatat cagtcaatgt ggat                                          24

<210> SEQ ID NO 16
<211> LENGTH: 25
<212> TYPE: DNA
<213> ORGANISM: Homo sapiens
<220> FEATURE:
<221> NAME/KEY: misc_feature
<222> LOCATION: (1)..(25)
<223> OTHER INFORMATION: TNFSF-8 Reverse Primer

<400> SEQUENCE: 16
gaagatggac aacacattct caaga                                         25

<210> SEQ ID NO 17
<211> LENGTH: 23
<212> TYPE: DNA
<213> ORGANISM: Homo sapiens
<220> FEATURE:
<221> NAME/KEY: misc_feature
<222> LOCATION: (1)..(23)
<223> OTHER INFORMATION: TNFSF-9 Forward Primer

<400> SEQUENCE: 17
agctacaaag aggacacgaa gga                                           23

<210> SEQ ID NO 18
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: TNFSF-9 Reverse Primer

<400> SEQUENCE: 18
cgcagctcta gttgaaagaa gaca                                          24

<210> SEQ ID NO 19
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: TNFSF-12 Forward Primer

<400> SEQUENCE: 19
tactgtcagg tgcactttga tgag                                          24

<210> SEQ ID NO 20
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: TNFSF-12 Reverse Primer

<400> SEQUENCE: 20
cgcagtggct gagaattcct                                               20

<210> SEQ ID NO 21
<211> LENGTH: 22
```

```
<212> TYPE: DNA
<213> ORGANISM: Homo sapiens
<220> FEATURE:
<221> NAME/KEY: misc_feature
<222> LOCATION: (1)..(22)
<223> OTHER INFORMATION: TNFSF-13 Forward Primer

<400> SEQUENCE: 21
atatggtgtc cgaatccagg at                                              22

<210> SEQ ID NO 22
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: TNFSF-13 Reverse Primer

<400> SEQUENCE: 22
cctgacccat ggtgaaagtc a                                               21

<210> SEQ ID NO 23
<211> LENGTH: 25
<212> TYPE: DNA
<213> ORGANISM: Homo sapiens
<220> FEATURE:
<221> NAME/KEY: misc_feature
<222> LOCATION: (1)..(25)
<223> OTHER INFORMATION: TNFSF-13B Forward Primer

<400> SEQUENCE: 23
atgcctgaaa cactacccaa taatt                                           25

<210> SEQ ID NO 24
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: TNFSF-13B Reverse Primer

<400> SEQUENCE: 24
gcaagttgga gttcatctcc ttct                                            24

<210> SEQ ID NO 25
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: TNFSF-14 Forward Primer

<400> SEQUENCE: 25
cgtccgtgtg ctggatga                                                   18

<210> SEQ ID NO 26
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: TNFSF-14 Reverse Primer

<400> SEQUENCE: 26
catgaaagcc ccgaagtaag ac                                              22
```

```
<210> SEQ ID NO 27
<211> LENGTH: 23
<212> TYPE: DNA
<213> ORGANISM: Homo sapiens
<220> FEATURE:
<221> NAME/KEY: misc_feature
<222> LOCATION: (1)..(23)
<223> OTHER INFORMATION: TNFSF-15 Forward Primer

<400> SEQUENCE: 27
tgcgaagtag gtagcaactg gtt                                                23

<210> SEQ ID NO 28
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: TNFSF-15 Reverse Primer

<400> SEQUENCE: 28
ccattagctt gtccccttct tg                                                 22
```